United States Patent
Fontenot et al.

[11] Patent Number: 5,879,306
[45] Date of Patent: *Mar. 9, 1999

[54] INFRARED SYSTEM FOR VISUALIZING BODY MEMBERS

[75] Inventors: Mark G. Fontenot, Lafayette, La.; Richard Feinberg, Bellingham, Wash.

[73] Assignee: Stryker Corporation, Santa Clara, Calif.

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,517,997.

[21] Appl. No.: 748,412

[22] Filed: Nov. 13, 1996

Related U.S. Application Data

[60] Provisional application No. 60/020,473 Jun. 13, 1996.

[51] Int. Cl.$^6$ ............................................. A61B 5/00
[52] U.S. Cl. ............................. 600/473; 600/476
[58] Field of Search ................................. 128/664, 665, 128/899, 653.1, 634; 606/32, 34, 41, 15; 348/71, 65; 600/473, 476, 342, 407

[56] References Cited

U.S. PATENT DOCUMENTS

| | | | |
|---|---|---|---|
| 4,470,407 | 9/1984 | Hussein | 128/6 |
| 4,898,175 | 2/1990 | Noguchi | 128/634 |
| 4,961,738 | 10/1990 | Mackin | 606/15 |
| 5,090,959 | 2/1992 | Samson et al. | 604/96 |
| 5,104,392 | 4/1992 | Kittrell et al. | 606/15 |
| 5,187,572 | 2/1993 | Nakamura et al. | 358/98 |
| 5,423,321 | 6/1995 | Fontenot | 128/664 |
| 5,517,997 | 5/1996 | Fontenot | 128/664 |
| 5,594,497 | 1/1997 | Ahern et al. | 348/71 |
| 5,636,644 | 6/1997 | Hart et al. | 128/897 |

*Primary Examiner*—William E. Kamm
*Assistant Examiner*—Eleni Mantis Mercader
*Attorney, Agent, or Firm*—Howard L. Rose

[57] ABSTRACT

The present invention provides a method and apparatus for illuminating the region of a body member to be subjected to a surgical procedure by inserting an infrared conducting fiber into the body member, the fiber emitting infrared light energy over a limited range at the precise location where the procedure is to occur. The procedure may involve an organ, a blood vessel, even a nerve. Mechanisms and detectors may be employed to locate the infrared emissions.

16 Claims, 5 Drawing Sheets

INFRARED SYSTEM FOR VISUALIZING BODY MEMBERS

CROSS-REFERENCE TO RELATED APPLICATIONS

This application converts Provisional Application No. 60/020,473 filed Jun. 13, 1996, into a nonprovisional application.

This application is also related to application Ser. No. 08/663,015 filed Jun. 7, 1996 which is a continuation-in-part of U.S. patent application Ser. No. 08/472,785 filed Jun. 7, 1995. It is also related to U.S. patent application Ser. No. 08/355,164 filed Dec. 8, 1994, which is a continuation-in-part of U.S. patent application Ser. No. 08/305,296 filed Sep. 15, 1994 now U.S. Pat. No. 5,517,997; and U.S. patent application Ser. No. 08/190,516 filed Feb. 2, 1994 now U.S. Pat. No. 5,423,321, which was a continuation-in-part of U.S. patent application Ser. No. 08/016,565 filed Feb. 11, 1993 (now abandoned).

STATEMENT REGARDING FEDERALLY SPONSORED RESEARCH OR DEVELOPMENT

Not Applicable

FIELD OF THE INVENTION

The present invention provides a system and method for locating and visualizing body members and more particularly to the use of infrared light emitters and catheters for locating and rendering visible body members subject to a surgical or investigative procedure.

BACKGROUND OF THE INVENTION

U.S. Pat. Nos. 5,423,321 and 5,517,997, the latter assigned to the assignee of the present invention, disclose the use of an infrared emitter and infrared detector for visualizing and thus permitting determination of location of body members to be protected or managed during a surgical procedure adjacent such member.

The subject matter of the aforesaid patents as related to equipment employed in such procedures is incorporated herein by reference.

As indicated above, the prior efforts in this field have been related essentially to protecting or managing members by locating them. These efforts were not related to precisely locating and identifying the region of members to be involved in the procedures.

OBJECTS OF THE INVENTION

It is an object of the present invention to use infrared emitters and detectors for identifying a body member subject to a surgical procedure and to clearly identify the location of the region to be involved in the procedure.

Another object of the present invention is to identify blood vessels involved in a surgical procedure and to precisely locate the region of the vessel involved in the procedures.

It is yet another object of the invention to use infrared light energy to locate the region of the esophagus on which a procedure such as Nissen Fundoplication is to be performed.

It is still another object of the present invention to provide low temperature transillumination of a blood vessel, esophagus, rectum, rectosigmoid and other organs during laparoscopy, thoracoscopy or open surgical procedures.

BRIEF SUMMARY OF THE PRESENT INVENTION

In accordance with the present invention an infrared illuminated Bougie is intended to aid in the identification and definition of the precise location of a region of the esophagus, rectum, rectosigmoid or other body structures on which a surgical procedure is to be performed. The use of infrared has several advantages related to low temperature and ability to detect the infrared light energy location to the exclusion of visual light.

The system employs a catheter (Bougie) together with a source of infrared light, a fiber for conducting the light and in the region of the operation or other procedure emitting the light transversely or axially from the fiber, an infrared detector coupled to an audible indicator and sounding an alarm when close to the source, and an infrared system for imaging the surgical site on a video monitor.

Similarly the location of a surgical site involving an artery or vein to be operated upon may be precisely located. As an example, if a kidney is to be removed, the main arteries and veins to the kidney must be located and ligated. In order to distinguish the renal artery from the ureter, for instance, the ureter is transilluminated with infrared light energy as taught by the aforesaid patents permitting ready distinction from the renal artery. Once the renal artery has been distinguished from the ureter, an infrared light emitting fiber can then be safely inserted into the proper lumen and the ureter source turned off to clearly define the artery. In the alternative, the two light sources can be modulated at different frequencies to readily distinguish the two structures.

In a further embodiment a guide wire is placed in the renal artery or vein to the kidney to guide a catheter into the proper location and then the infrared emitting fiber may be inserted. Similar techniques are used to harvest a saphenous vein section to be used in coronary artery by-pass surgery. Usually the display system of the present invention uses a color video monitor. When doing vein harvesting a black & white video camera is employed since it is more sensitive to infrared light than a color video camera. The black and white video camera is cheaper, more sensitive and can be mounted from the ceiling over the leg.

It should be noted that to indicate a precise location in any of these procedures the infrared emitting fiber may contain or have an X-ray absorbent material such as gadolinium at a precise predetermined location.

The efficiency of the system may be increased by using a balloon catheter having the balloon positioned over the infrared emitting segment of the emitting fiber. The balloon is inflated resulting in occlusion of the blood to create a light path between the emitting fiber and the blood vessel wall essentially devoid of blood. The inflated balloon also thins the blood vessel wall providing less scattering or absorption of the light resulting in improved transmission of light of all spectra across the wall of the vessel.

The above and other features, objects and advantages of the present invention, together with the best means contemplated by the inventor thereof for carrying out the invention will become more apparent from reading the following description of a preferred embodiment and perusing the associated drawings in which:

DETAILED DESCRIPTION OF THE PRESENT INVENTION

Figure 1:
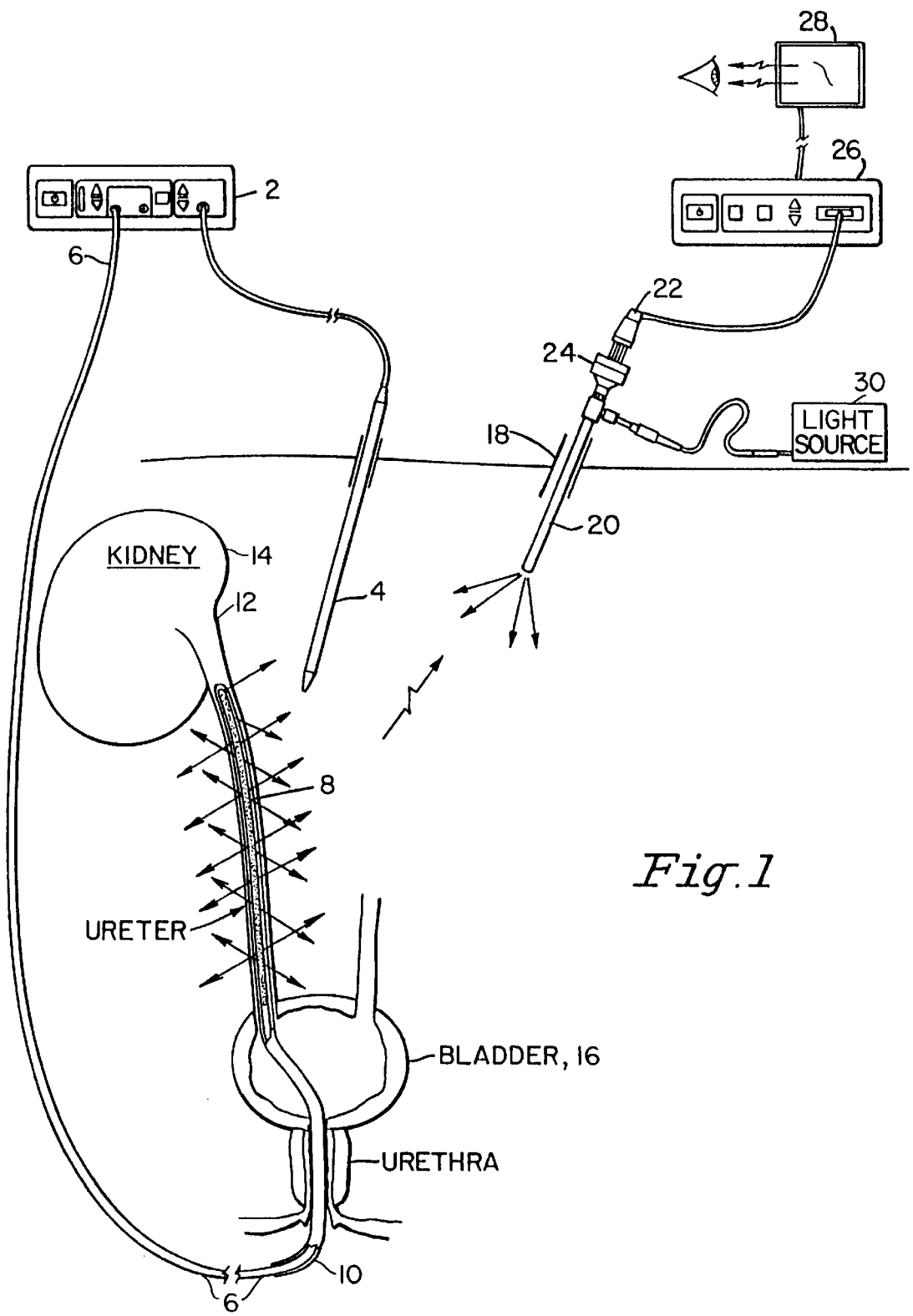
FIG. 1 is a schematic view of the apparatus of the present invention employed to illuminate the region surrounding a ureter with infrared light detected by the instruments illustrated.

Referring initially to FIG. 1 of the accompanying drawings the equipment to be employed in practicing the present invention is illustrated. An illuminator 2 includes, for instance, an infrared emitting laser diode and a detector probe 4 for detecting infrared light energy. Infrared light energy generated by the laser diode is provided to a light fiber 6 that is abraded or otherwise structured over a region 8 adjacent its end to emit light energy transverse to its longitudinal dimension. In FIG. 1 the light emitting fiber 6 is positioned in a catheter 10 which in this instance is located in ureter 12 extending between kidney 14 and bladder 16.

Infrared light energy emitted by fiber 6 is detected by detector probe 4 when located sufficiently near to the ureter and in this instance produces an audible sound thus defining the location of the ureter. An endoscope 20 may be inserted into the region through a trocar 18 as is probe 4. An IR sensitive laparoscopic video camera 22, coupled to the endoscope 20 through an optical coupler 24 views the surgical site and supplies information to camera control unit 26 and thence to monitor 28. Visible light is supplied to the endoscope from a source 30 which may be filtered to be IR free and color compensated with a Hoya EM500 filter or the like to illuminate the surgical site. The video camera 22 displays on the video monitor 28 the surgical site and the location of the probe 4. Audible soundings by unit 2 coupled with the visual display of the probe permits accurate location of the ureter.

Figure 2:
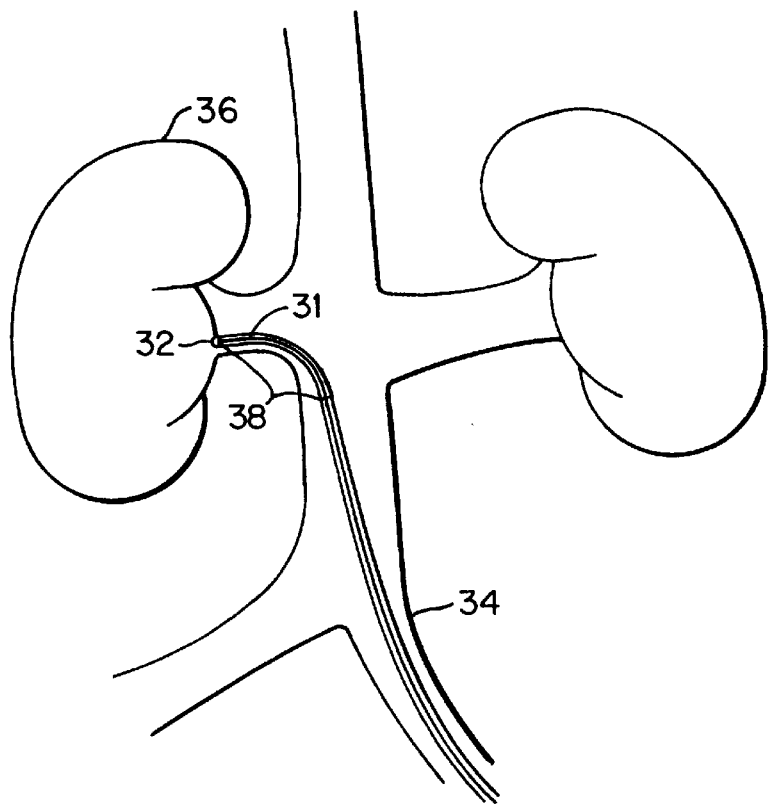
FIG. 2 illustrates the use of a balloon catheter and infrared emitting fiber to identify the region of a vessel to be severed from a kidney to be removed.

Referring now to FIG. 2 of the drawings, an emitting fiber 31 is positioned in a balloon catheter 32 positioned in the lumen of a renal artery 34 of a kidney 36. The fiber carries radiopaque markers 38 to assist in accurately indicating the position of the fiber in the artery 34 using X-ray fluoroscopy. The fiber is extended to the exact location of the vessel 34 adjacent to the kidney 36 to be removed.

Figure 3:
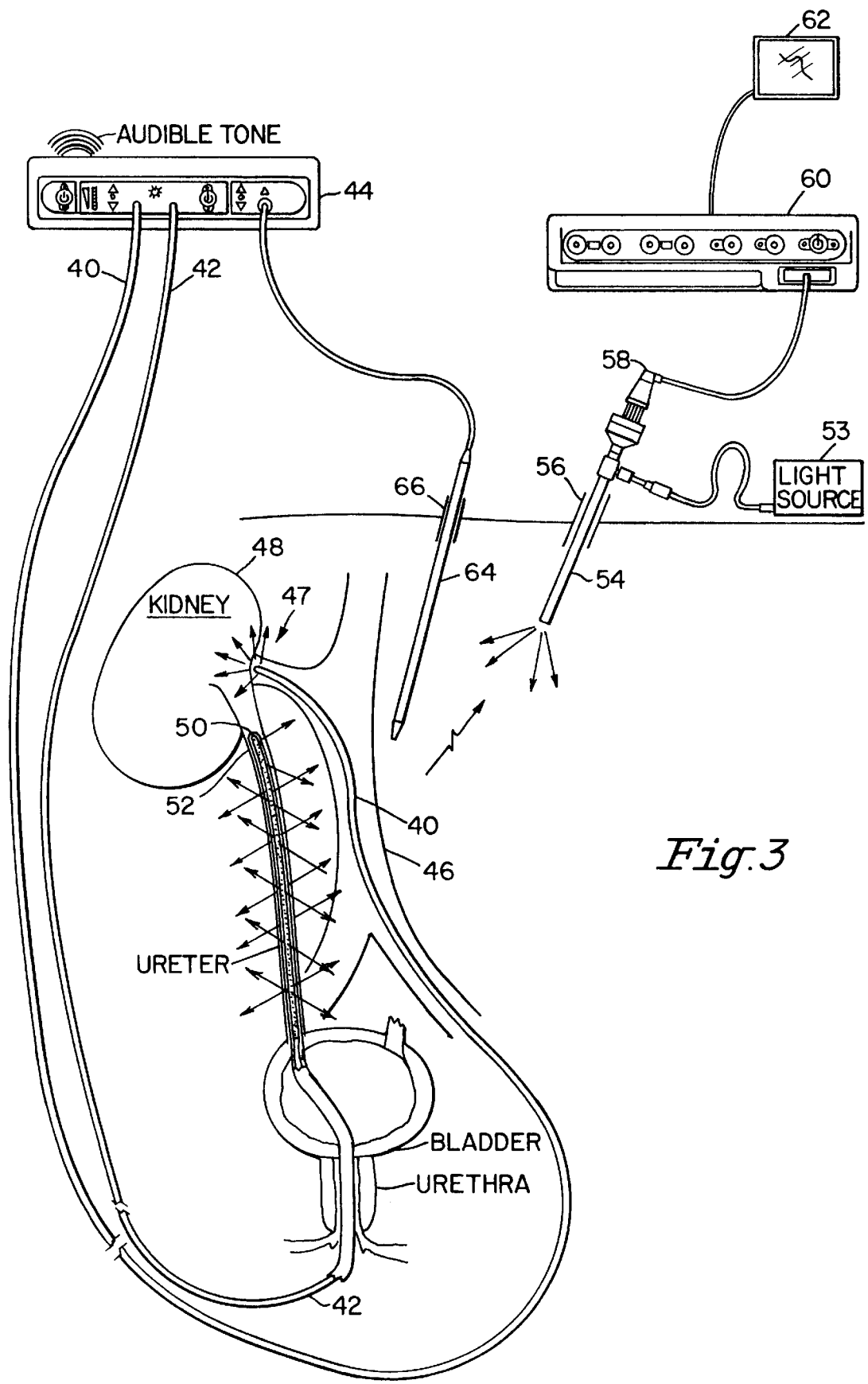
FIG. 3 is a schematic diagram of the combination of the arrangements of FIGS. 1 and 2.

Referring now to FIG. 3 of the drawings the entire arrangement for providing a view of the renal artery at the point at which it is to be severed is illustrated. Two light emitting fibers 40 and 42 receive infrared light energy from an illuminator 44. Fiber 40 is inserted into a vascular catheter in turn inserted into renal artery 46. The fiber is positioned so as to emit infrared light energy at the point 47 at which the artery is to be severed from kidney 48.

Fiber 42 has previously been inserted into ureter catheter 50 to clearly define the location of ureter 52 to insure that the fiber 40 and its associated renal catheter are now inserted in the ureter 52. The site is illuminated with light in the visual range from source 53 through endoscope 54 introduced in this instance through trocar 56. The endoscope supplies a view of the field to laparoscopic video camera 58. After processing in control unit 60, the site is displayed on a video monitor 62 together with a view of detector probe 64.

Laparoscopic nephroureterectomy (LN) is a minimally invasive procedure in which a diseased or non-functioning kidney is removed through a series of ports and small incisions. There are several difficult aspects of LN, two of which involve identifying the ureter and renal artery-vein complex. It is not uncommon for a surgeon to spend up to 45 minutes attempting to endoscopically locate the renal artery-vein complex during a LN. The surgeon can use the present system to identify and manage the renal artery-vein complex.

There are two methods with which to place the catheter into the renal artery. The first method is a traditional technique of placing any vascular catheter into the renal artery or renal vein which invokes commonly used techniques of vascular catheter placement under fluoroscopic control. The second method according to the present invention allows placement of the catheter in the renal artery under electronic control using either the detector probe or the imaging system just disclosed or a combination thereof.

Several methods and devices are used to detach the vascular system from the kidney.

In one such method the imaging video system detects and displays the infrared transilluminated ureter and/or renal artery (or renal vein) onto the video monitor. During difficult surgical cases when the renal artery-vein complex is embedded in dense fibrous tissue, the detector probe 64 can be introduced into the surgical site through a trocar 66. Visualization of the detector probe tip on the video monitor allows the surgeon to position the detector probe in the approximate area of the renal artery-vein complex. The detector probe is maneuvered until an audible sound is broadcast from the illuminator 44 which indicates detection of the infrared transilluminated renal artery (or renal vein). The imaging video system can be used to detect and accurately locate the probe 40 and thus the renal artery-vein complex.

From FIG. 3, there are two methods that can be employed to ascertain whether the detected structure is the renal artery (or renal vein) or ureter. In the first, suppose the surgeon elects to locate the renal artery (or renal vein) using the detector probe. After locating the ureter, the surgeon simply disconnects the emitting fiber to the ureter at the illuminator 44, thus leaving the infrared laser light power being delivered to the emitting fiber in the renal artery (or vein) only. The imaging video system or detector probe is used to detect the renal artery (or renal vein) in the same manner as described above.

The second method involves differing the output modulation of the two infrared channels of the illuminator 44. The wavelength and/or modulation of each diode can be set differently. Then, the surgeon selects the modulation/frequency in the detector probe circuitry that will detect the output of a particular laser diode. The surgeon introduces the detector at the surgical site and searches for a predetermined infrared signal until an audible tone is broadcast from the illuminator which indicates detection of the infrared transilluminated structure.

Figure 4:
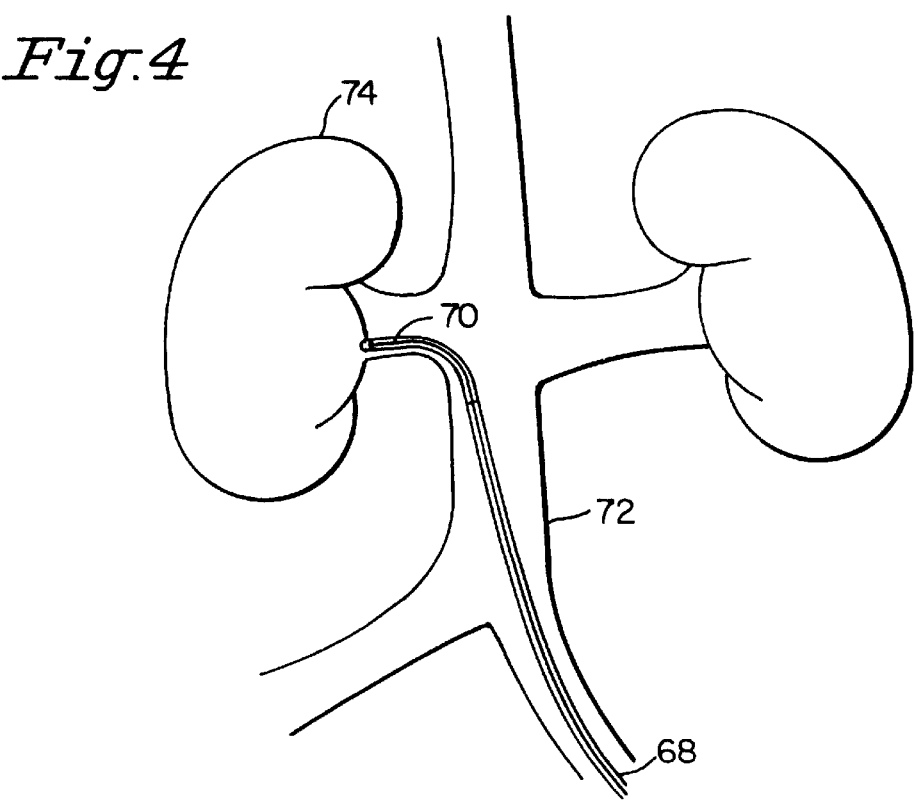
FIG. 4 illustrates the use of a guide wire to position a catheter and emitting fiber.

Referring to FIG. 4 a catheter 68 is placed at the renal artery or vein using a guide wire 70. The use of guide wires is a common technique for placing catheters in the vascular system. Under fluoroscopic control, the guide wire is placed in the renal artery or vein next to the kidney. The catheter can have a lumen that will allow the catheter 68 to be passed over the guide wire 70 and into a renal artery 72 or vein next to the kidney 74.

Radiopaque markers are placed on the catheter in order to improve the visibility of the catheter under fluoroscopy.

Figure 5:
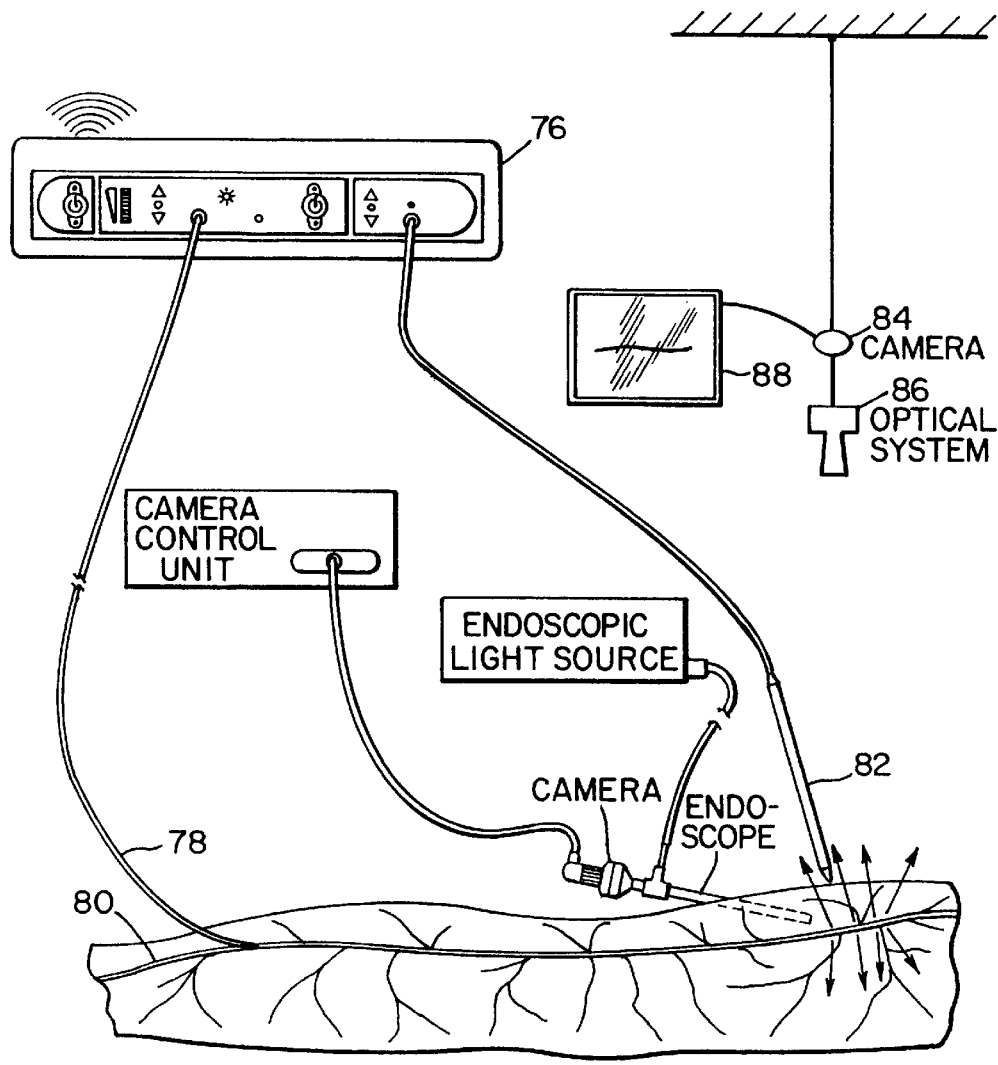
FIG. 5 illustrates an arrangement for harvesting a vein from a leg of the patient or a donor.

Referring now to FIG. 5 of the accompanying drawings, the apparatus for the method of vein harvesting is disclosed. Vein harvesting can be performed either endoscopically or using an open surgical technique. Illuminator 76 supplies infrared light to a fiber inserted into a catheter placed in the lumen of the saphenous vein. In the conventional open surgical approach, the detector probe is used to trace the emitting segment of the fiber within the saphenous vein as the fiber is moved to and fro in the catheter. A marking pen is used to mark the position of the vein on the leg. An alternative method can be invoked by employing an overhead color or black and white video camera which images the leg and infrared transilluminated saphenous vein on a video monitor. The endoscopic approach uses an endoscope coupled to an optical coupler and video camera. The endoscope is introduced into the leg through the skin via a skin incision. The surgeon tracks the endoscope along the infrared transilluminated saphenous vein. Harvesting the saphenous vein proceeds using surgical techniques which dissect the vein from the surrounding tissue, cutting and ligating ancillary venous branches, the removing the vein from the leg for grafting.

Figure 6:
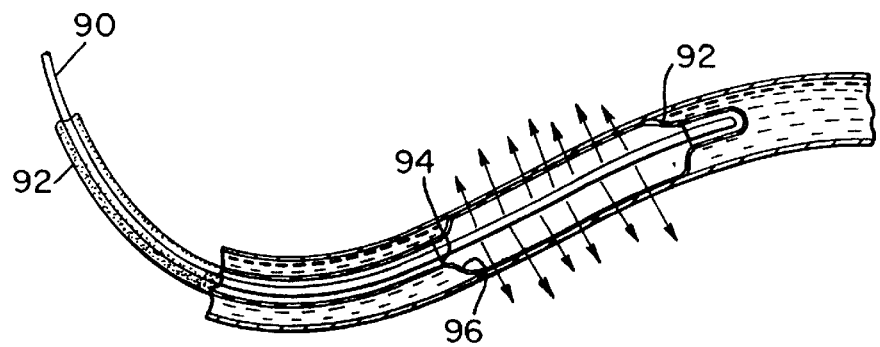
FIG. 6 illustrates the use of a balloon catheter in a procedure involving a blood vessel.

Referring to FIG. 6 of the drawings, a procedure for enhancing the infrared output from a vessel is disclosed. Such is important particularly with use of infrared since the illuminator employed herein only puts out up to 500 mW. An optic fiber 90 is disposed in a balloon catheter 92. Radiopaque material 94 is incorporated at the end of the balloon to mark the beginning of the balloon region 96 of the catheter. The balloon is expanded to exclude blood and/or expand the vessel to thin its adjacent wall. As a result of elimination of the absorption of light normally resulting from the presence of blood and thinning the vessel walls, the infrared light energy emitted from the vessel is significantly increased.

Figure 7:
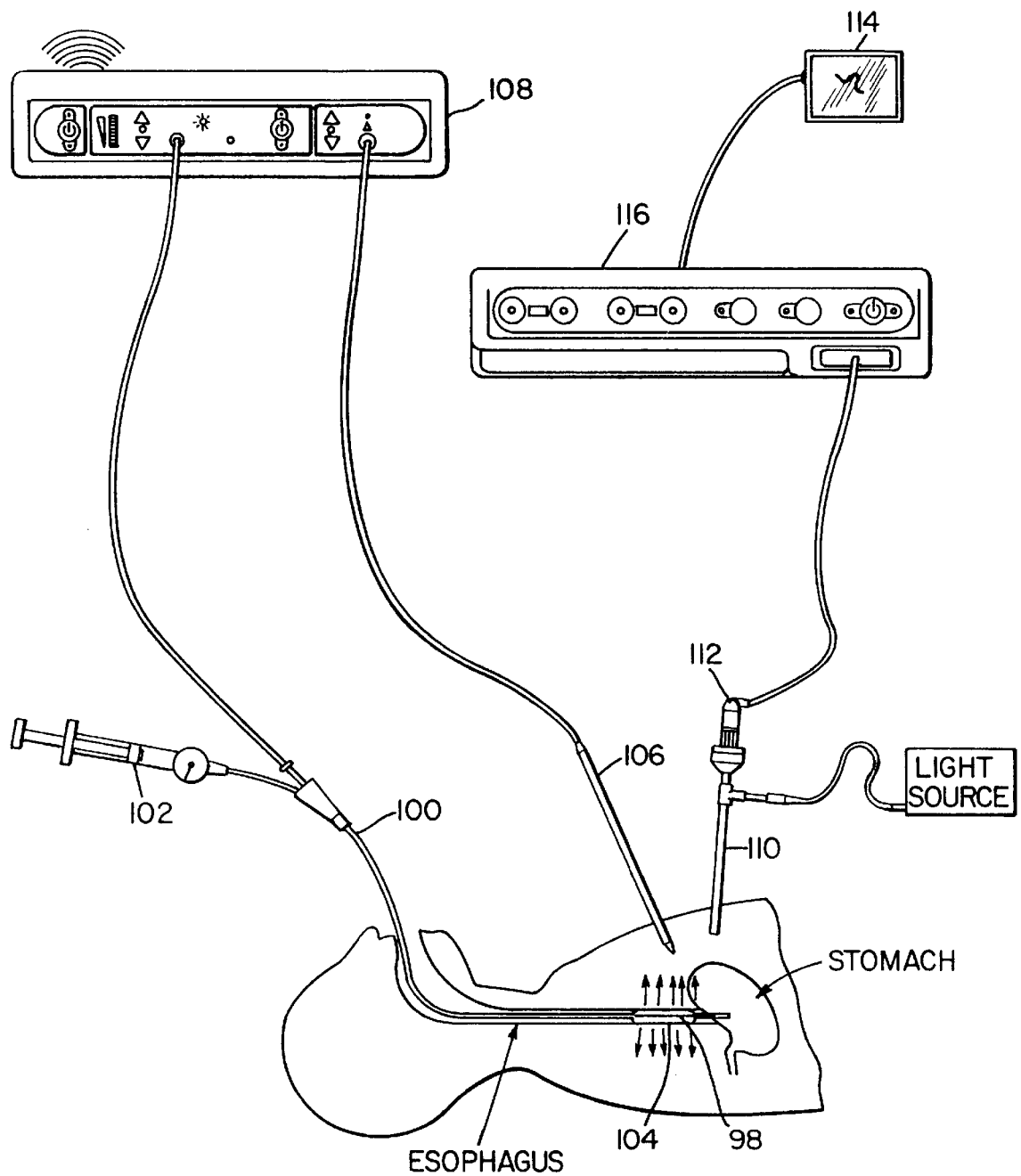
FIG. 7 illustrates the instrumentation employed in performing a Nissen Fundoplication.

Referring now to FIG. 7 of the drawings, the use of the equipment of FIG. 3 in a Nissen Fundoplication procedure is described. The procedure so far as the human anatomy is concerned is known, the use of the equipment described herein is not. In this procedure a region of the stomach is wrapped around the esophagus to in effect form a girdle around the esophagus. Management and identification of the esophagus during laparoscopic Nissen Fundoplication is especially important because of its inherent fragility and susceptibility for iatrogenic perforation or damage.

An infrared emitting fiber 98 is inserted into a balloon catheter 100 positioned in the esophagus and extending to the junction of the esophagus and the stomach. A pump 102 is used to inflate balloon 104 with fluid. The fluid may contain small Teflon® particles of the order of 0.5 to 5 microns which act to scatter light. The fiber emits infrared light energy clearly defining the region of the procedure. As in prior uses described above, a detector probe 106 is coupled to illuminator 108 that produces an audible sound upon the probe approaching the infrared emitting fiber. An endoscope 110 is also inserted into the region adjacent the operative site and transmits light including infrared light to endoscopic video camera 112. The images formed by the video camera 112 are transmitted to a video monitor 114 via a control unit 116. During the procedure the balloon of the catheter is inflated and visualization is provided by the video camera and video monitor with or without the assistance of the detector probe 106.

Just prior to suturing the gastric wrap, the balloon is inflated to the predetermined size using the pump. The emitting segment of the emitting fiber coincides with the balloon so the surgeon can correctly position the balloon at the level of the gastric wrap prior to inflation. Inflating the balloon to the predetermined diameter allows the surgeon to wrap and suture the stomach around the esophagus. In addition, the tension in the gastric wrap or the gastric wrap pressure can be measured and recorded from the pressure gauge of the pump as the difference between the resting inflation of the balloon and the final wrap pressure.

If the light produced by a 500 mW laser is insufficient in this or any other procedure involving particularly the illumination of a body member that is the subject of the procedure being performed, the two fibers illustrated in FIG. 3 may both be placed in such body member thus doubling the infrared light output. The fibers can be quite small. Another advantage of the present invention is that even at maximum power output, 500 mW, the temperature rise of the fiber is about 0.6° C. whereas visible light of sufficient wattage to be effective produces a temperature rise of 20.6° C.

Once given the above disclosure, many other features, modifications and improvements will become apparent to the skilled artisan. Such features, modifications and improvements are, therefore, considered to be a part of this invention, the scope of which is to be determined by the following claims.

We claim:

1. A method of illuminating a precise location of a body part to be subjected to a surgical procedure comprising the steps of inserting a catheter into the body part to at least the location, of the procedure, inserting into the catheter an infrared light conducting member to emit infrared light to a region limited to immediately adjacent the location at which surgery is to occur, connecting the member to a source of infrared light, and detecting the location of the infrared light emitted by said member.

2. The method according to claim 1 wherein the catheter is a balloon catheter further comprising inflating the balloon catheter to assist in the process of locating the balloon.

3. A method of defining precisely the location of a procedure to be conducted on a member of a body of a living or previously living creature comprising the steps of inserting into the body an infrared emitting fiber that emits infrared over an area approximately that of the area of the procedure, attaching the fiber to a source of infrared light energy, locating the fiber such as to illuminate with infrared light energy emitted from the fiber substantially only the precise location of the member at which a procedure is to be conducted, and determining the location of emission of the infrared light energy from the member.

4. A method according to claim 3 further comprising the step of including in the fiber an X-ray opaque material.

5. A method according to claim 4 further comprising employing X-ray detecting equipment to locate the X-ray opaque material, and maneuvering the fiber to position the X-ray opaque material in a position to cause the infrared emitting region of the fiber to be located at the precise location.

6. A method according to claim 3 further comprising the steps of
  inserting a catheter into the member to be subjected to a procedure, and
  inserting the fiber into the catheter.

7. A method according to claim 3 further comprising the steps of
  inserting a balloon catheter into the member that is to be subjected to a procedure,
  locating the balloon generally in the region of the procedure,
  inserting the fiber into the catheter,
  inflating the balloon, and
  locating the fiber so as to emit infrared light energy at the precise location of the procedure.

8. A method according to claim 3 further comprising the steps of
  inserting an infrared light conductor and emitter into a body to illuminate such body immediately adjacent a surgical site.

9. Apparatus for precisely locating a surgical site comprising,
  an infrared conducting fiber having an end region for emitting a narrow beam of infrared light,
  a source of infrared light connected to supply infrared light to said fiber,
  a catheter for insertion into a body structure to have a surgical procedure performed thereon at a precise location of the body,
  means for inserting said fiber into said catheter and locating the end region of said fiber to cause the narrow beam of infrared to be directed substantially only at the precise location of the surgery, and
  means for detecting the precise location of the infrared emitted by said fiber.

10. The method according to claim 9 further comprising
  viewing the surgical site with a camera sensitive to both infrared light energy and visible light energy.

11. An apparatus according to claim 9 further comprising
  a source of white light devoid of infrared light directed into the surgical site, and
  a camera for viewing said white and infrared light.

12. An apparatus according to claim 9 further comprising
  a guide wire adapted to be inserted into the body to the location to be subject to a surgical procedure, and
  means for guiding the fiber along said guide wire.

13. An apparatus according to claim 9 further comprising
  an X-ray blocking material at a predetermined location in said fiber, and
  means for determining the location of said blocking material in said fiber.

14. An apparatus according to claim 9 wherein
  said catheter is a balloon catheter,
  means for locating the balloon at a location including the region to be subjected to a surgical procedure,
  means for inflating said balloon, and
  means for locating the infrared emitting region of said fiber in the region of the balloon.

15. An apparatus according to claim 9 wherein said body is a blood vessel.

16. Apparatus for precisely locating a surgical site comprising,
  an infrared conducting fiber having an end region for emitting infrared light over a narrow region,
  a source of infrared light connected to supply infrared light to said fiber,
  a catheter for insertion into a body structure to have a surgical procedure performed thereon at a precise location of the body,
  means for locating the end region of said fiber at said precise location, and
  means for detecting the location of the infrared emitted by said fiber.

* * * * *